United States Patent [19]

Karimi et al.

[11] Patent Number: 5,084,315

[45] Date of Patent: Jan. 28, 1992

[54] LUBRICIOUS COATINGS, MEDICAL ARTICLES CONTAINING SAME AND METHOD FOR THEIR PREPARATION

[75] Inventors: Houshang Karimi; Stanley C. Wells, both of Centerville; David E. Spielvogel, Springboro; Mutlu Karakelle; Robert A. Taller, both of Centerville, all of Ohio

[73] Assignee: Becton, Dickinson and Company, Franklin Lakes, N.J.

[21] Appl. No.: 473,506

[22] Filed: Feb. 1, 1990

[51] Int. Cl.$^5$ .................. B29D 23/00; A61L 15/50; D01D 5/24
[52] U.S. Cl. ................. 428/36.6; 428/36.91; 428/411.1; 428/424.6; 428/500; 428/423.1; 427/2; 264/209.1; 264/171
[58] Field of Search .............. 428/35.7, 36.6, 36.91, 428/413, 424..2; 264/171, 209.1; 604/266, 8, 280

[56] References Cited

U.S. PATENT DOCUMENTS

| | | | |
|---|---|---|---|
| 4,062,834 | 12/1977 | Gilding et al. | 200/77 A |
| 4,100,309 | 7/1978 | Micklus et al. | 427/2 |
| 4,373,009 | 2/1983 | Winn | 428/424.2 |
| 4,642,267 | 2/1987 | Creasy et al. | 428/413 |
| 4,720,521 | 1/1988 | Spielvogel et al. | 524/862 |
| 4,767,414 | 8/1988 | Williams et al. | 604/230 |
| 4,876,126 | 10/1989 | Takemura et al. | 428/35.7 |

Primary Examiner—James J. Seidleck
Assistant Examiner—Charles R. Nold
Attorney, Agent, or Firm—Richard E. Brown

[57] ABSTRACT

An article which becomes lubricious when wet includes a base polymer and a coating composition thereon. The composition includes a lubricating polymer and a matrix polymer which adheres to the base polymer and serves as a carrier for the lubricating polymer. The composition may also include a homogenizing polymer to enhance the compatibility of the matrix and lubricating polymer. The invention includes a method to make the article of the invention by coextruding the base polymer and the coating composition.

24 Claims, No Drawings

LUBRICIOUS COATINGS, MEDICAL ARTICLES CONTAINING SAME AND METHOD FOR THEIR PREPARATION

BACKGROUND OF THE INVENTION

1. Field of the Invention

This invention relates to lubricated surfaces. More particularly, the invention relates to a coating which is lubricious and biocompatible and to a method for its application to an article surface.

2. Background

Many articles, devices and products require a lubricated surface. In the medical instrumentation and diagnostic field, simple sensing devices such as, for example, thermometers and needles, or electrode components of complex monitoring apparatuses, must be inserted into a body cavity or through the skin and at a later time withdrawn. Patient treatment often includes catheterization procedures or nutrition delivery systems, most of which involve invasive techniques. In all such cases, effective lubrication which is stable throughout both the insertion and withdrawal stages of the procedure contributes greatly to patient comfort.

Many medical devices are fabricated from glass or polymeric materials such as polypropylene, polyvinyl chloride, polytetrafluoroethylene and polyurethane. Such materials are for the most part inherently nonlubricious. A variety of approaches to introduce lubricity have been advanced. Simple coatings of lubricants such as mineral oils or silicones to glass or polymeric surfaces are generally unsatisfactory because the surface energy is too low and the lubricant tends to migrate or "bead." A method to overcome migration and beading of silicone lubricants is described by Williams et al. in U.S. Pat. No. 4,767,414. A surface to be lubricated is coated with silicone oil and both the surface and oil are subjected to an ionizing plasma.

Spielvogel et al., in U.S. Pat. No. 4,720,521 teaches adherence of a lubricating composition to a surface. The composition includes a polysiloxane lubricant entrapped in a mixture of a plurality of reactive silicone components which, on curing, adhere to the surface.

Polyurethanes have demonstrated particular advantages, such as resistance to thrombogenesis, for fabrication of medical devices, and have been used both as a substrate and as a coating on a polymeric substrate. Polyurethanes prepared from high molecular weight polyether glycols are conventionally referred to as polyetherurethanes.

Polyetherurethane compositions develop microdomains conventionally termed hard segment domains and soft segment domains and are often referred to as segmented polyurethanes. They are (AB)n type block copolymers, A being the hard segment and B the soft segment. The hard segment domains form by localization of the portions of the copolymer molecules which include the isocyanate and extender components whereas the soft segment domains form from the polyether glycol portions of the copolymer chains. The phase separated microdomain structure forms if the hard segments of the polyetherurethane chain are a certain size. A long hard segment promotes the phase separated microdomain structure. Conversely, non-extended formulations (those lacking an extender) have very short hard segments and minimum phase separated microdomain structure. The hard segment is crystalline and provides physical crosslinking and reinforcement whereas the soft segment is mostly in a rubbery state and provides elasticity.

Elastomeric segmented polyurethanes have particular advantages for fabrication of medical devices, as discussed by Gilding et al. in U.S. Pat. No. 4,062,834 but have limited inherent lubricity. Micklus et al. in U.S. Pat. No. 4,100,309 teaches a lubricious polyurethane-polyvinylpyrrolidone (PVP) interpolymer coating which may be applied to a polymeric article by dipping the article into a solvent solution of polyurethane and a polyisocyanate to give an isocyanate-containing prepolymer on the article surface and dipping the prepolymer coated article into a solution of PVP.

In U.S. Pat. No. 4,373,009 to Winn, a substrate surface is primed with a polyisocyanate as shown by Micklus et al., and the isocyanate groups are covalently bonded to active hydrogens of a hydrophilic copolymer, such as a copolymer of PVP and acrylamide. A coating which is stable and resistant to removal, in contrast to prior art coating, is claimed.

U.S. Pat. No. 4,642,267 to Creasy et al. describes lubricious coatings which are alloys or blends of PVP and polyurethanes lacking both free isocyanate groups and chain extenders.

Copending application Ser. No. 347,133, of common assignee with the present invention, discloses a blend of a hydrophilic polyurethane and PVP and a method to render an article surface lubricious by dipping the article in a solvent solution of the blend.

Although the above disclosures have advanced the art of rendering surfaces lubricious, there remains a need for a coating which is instantly lubricious, easily applied without solvent and strongly adherent so as to remain on the substrate to which it is applied with no tendency to wash off or separate as solid flakes on prolonged contact with liquids.

SUMMARY OF THE INVENTION

One aspect of the present invention is a medical article which is lubricious when wet comprising a base polymer and a coating composition thereon. Preferred base polymers are polyurethane and polyvinyl chloride (PVC).

The coating composition comprises a hydrophilic lubricating polymer and a polymeric matrix material which adheres to the base polymer and serves as a carrier for the lubricating polymer. If the base polymer is PVC, the matrix material may preferably be an alloy of PVC and a polyurethane. If the base polymer is polyurethane, the matrix material may preferably be a second polyurethane. For some coating compositions, a homogenizing polyurethane may be included to enhance the compatibility of the lubricating polymer and carrier.

A second aspect of the invention is a method to make the article. The method includes coextruding a melt of the base polymer and a melt of the coating composition so that the base polymer is shaped and coated with a continuous adhered layer of the coating composition.

Thus, the invention provides a medical tubing which becomes instantly lubricious when wet. The tubing is made by an extrusion process which eliminates the need for potentially toxic solvents which may be difficult to remove completely. The components of the article are thermoplastic, elastomeric and have excellent melt processibility for ease and economy of manufacture of the article. The coating composition bonds well to the base polymer as a result of the compatibility of the components of the composition to each other and to the base polymer. The low coefficient of friction of the article allows easy insertion and positioning of the article into a patient's body cavity and relieves patient trauma by lowering injury to surrounding tissues.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

The present invention provides a shaped article formed of a base polymer coated with a composition which adheres strongly to the base polymer and gives a surface which is instantly lubricious when the surface is wet. The invention includes a method for fabricating the article in which the base polymer and the coating composition are coextruded so that a layer of the coating composition is laminated onto the base polymer.

Articles contemplated to fall within the scope of the present invention are those which can benefit from a low coefficient of friction when in contact with an aqueous fluid, such as a body fluid. Medical tubing is the preferred article of the invention. In particular, catheters for use in the gastrointestinal tract, for vascular or arterial access, nasotracheal draining and urology benefit from the type of low friction surfaces disclosed in the invention. The most preferred article is a suction catheter.

A variety of thermoplastic polymers may be used as base materials with the only limitation being that the base polymer must be coextrudable with the composition. Representative base polymers are polyolefins such as polypropylene and polyethylene. Preferred base polymers are polyurethanes, polyurethaneureas, and polyurethane polysiloxane block copolymers. The most preferred base polymer is PVC. The invention will be described in terms of the two preferred base polymers, PVC and polyurethane.

The polyurethanes which may serve as the base polymer (and as a component of the coating composition as described below) may be synthesized by conventional methods, as described in general in Example I. As known in the art, these polyurethanes may be prepared from isocyanates, polyglycols and chain extenders. Other reagents may be included for particular applications. Suitable diisocyanates are aromatic diisocyanates such as 4,4'-diphenylmethane diisocyanate (MDI), and aliphatic diisocyanates, as, for example, hexamethylene diisocyanate. The most preferred diisocyanate is MDI.

The polyglycol component may be a polyester glycol or preferably a polyether glycol. The polyether glycol may be polyethylene glycol (PEG), polypropylene glycol, polytetramethylene ether glycol (PTMEG) or mixtures thereof. The choice of glycol depends on whether the polyurethane is to be the base polymer, a matrix polymer or the homogenizing polymer as described below.

The chain extender may be water and/or a low molecular weight branched or unbranched diol, diamine or aminoalcohol of up to 10 carbon atoms or mixtures thereof. Representative nonlimiting examples of chain extenders are butanediol (BDO); ethylene glycol; diethylene glycol; triethylene glycol; 1,2 propanediol; 1,3-propanediol; 1,6-hexanediol; 1,4-bis hydroxymethyl cyclohexane, hydroquinone dihydroxyethyl ether, ethanolamine, ethylenediamine and hexamethylenediamine. Preferred chain extenders are 1,6-hexanediol, ethylenediamine, hexamethylenediamine and, most preferably, BDO.

The properties of a polyurethane, such as tensile strength, thermoplasticity, elongation and water absorption are determined largely by the composition and ratio of the hard and soft segments. In accordance with the invention, it has been found that, when the base polymer is a polyurethane, an article of satisfactory mechanical properties is obtained when the hard segment is about 20 to 75, preferably about 40%, and the soft segment is PTMEG alone or blended with about 50% PEG. Calculation of the component ratios to give the desired hard segment content necessary for the particular property and/or particular application is well within the purview of one skilled in the art.

When the base polymer is PVC, an article of satisfactory mechanical properties is obtained when the molecular weight of the PVC is about 30K (1,000) to 1MM (1,000,000), preferably about 50K to 200K.

The coating composition contains at least two and preferably three or more components. The first component is a hydrophilic lubricating polymer which provides lubricity to the coated article when wet, as described below. The lubricating polymer may be any extrudable polymer which absorbs water and migrates to the surface of the coating composition. Suitable hydrophilic polymers are, for example, polyacrylic acid, polyhydroxyalkyl acrylates and hydrophilic polymers based on polyethyleneoxide. The preferred hydrophilic lubricating polymer is polyethyleneoxide having a molecular weight of about 100K to 8MM, preferably about 200K to 4MM, most preferably about 300K to 2MM. Suitable polyethyleneoxides may be purchased from Union Carbide Corporation South Charleston, W. Va., under the trade name Polyox ®.

A second component of the coating composition is a polymeric matrix material which serves as a carrier for the lubricating polymer and as a binder to provide adherence of the coating composition to the base polymer. The nature of the matrix material depends on the base polymer and preferably includes a polyurethane, hereinafter referred to as the matrix polyurethane.

When the base polymer is PVC, the matrix material preferably is an alloy of PVC and the matrix polyurethane. The percentage of PVC in the alloy may be about 50 to 95, preferably about 60% (in the present disclosure, all percentages are by weight unless otherwise stated) and the matrix polyurethane may be a polyester or polyether polyurethane. A particularly preferred matrix alloy is a PVC-polyesterpolyurethane commercially available under the trade name Colorite ® (Colorite Plastics Co. Ridgefield, N.J.). Preferred Colorite ® alloys have a hardness of about 60A to 90A.

For some coating compositions, in particular those including substantially hydrophobic matrix materials such as Colorite ®, it is advantageous to include a homogenizing polyurethane to enhance the compatibility of the matrix material and the lubricating polymer. The homogenizing polyurethane preferably has a hard segment of about 20 to 75, preferably about 40%, and may preferably be synthesized from a diisocyanate, a diol extender and a mixture of glycols. Preferred homogenizing polyurethanes have a hard segment of MDI and BDO and a soft segment of PTMEG and PEG. The PTMEG may have a molecular weight of about 650 to 2900, preferably about 650, and the PEG may have a molecular weight of about 600 to 8000, preferably about 1450. The ratio of PTMEG to PEG may be about 20:80 to 80:20, preferably about 50:50.

Preferred coating compositions include about 50 to 90, preferably about 70% of Colorite ® matrix polymer alloy, about 5 to 25, preferably about 10% of lubricating polyethyleneoxide and about 5 to 25, preferably about 20% of homogenizing polyurethane.

When the base polymer is a polyurethane, the matrix material may be the matrix polyurethane alone. Matrix polyurethanes for use with polyurethane base polymers may be synthesized from diisocyanates and diol extenders as described above and from PTMEG, PEG and mixtures thereof as the glycol component. Preferred matrix polyurethanes for use with a polyurethane base polymer have a hard segment content of about 20 to 75, preferably about 55% wherein the soft segment includes from about 80 to 20% PTMEG and from about 20 to 80% PEG. In this embodiment of the invention, the base and matrix polyurethanes may be sufficiently compatible that a homogenizing polymer may not be needed.

While not wishing to be bound by any theory, it is believed, although not substantiated, that a matrix material which has a chemical structure similar to the base material adheres well to the base material. Thus, a matrix material which includes PVC adheres well to a PVC substrate and a polyurethane matrix material adheres well to a polyurethane substrate. For most articles of the invention formed of PVC or polyurethane as the base polymer, sufficient tensile strength and/or other physical properties are best achieved with a base polymer of high hardness. Such polymers may be substantially hydrophobic and have poor compatibility with a hydrophilic lubricating polymer. If the matrix material and lubricating polymer are not compatible, poor results are achieved on coextrusion. The disclosed invention overcomes this problem by providing an optional homogenizing polymer to provide a uniform blend of matrix material and lubricating polymer prior to extrusion.

The components of the coating composition may be combined prior to extrusion by any conventional technique as known in the art. For example, the components may be melt compounded in a Banbury mixer. Alternatively, a single or twin screw extruder is used to melt compound the components, extrude the melt through a die and pelletize the composition.

If desired, a conventional radiopaque material, such as barium sulfate or bismuth trioxide may be included in the base polymer prior to extrusion. The radiopaque may be in the form of stripes or may be incorporated throughout the base polymer. Inclusion of a radiopaque material in a polymer to be extruded is wholly conventional and well known to those skilled in the art, and no further details for this aspect of the invention are needed.

Coextrusion of the base polymer and the coating composition may be performed with any conventional and commercially available coextrusion equipment. Suitable coextrusion apparatus may be purchased, for example, from Genca Cable Company, Clearwater, Fla., or from Wayne Machine and Die Company, Totowa, N.J., or, if desired, custom coextrusion apparatus can be designed for fabrication of any specific article of the invention.

Uncoated PVC suction catheters heretofore used in medical practice have an average coefficient of friction of about 0.92 when determined in accordance with the procedure of Example IV. When coated by the solvent based polyvinylpyrrolidone composition disclosed in copending application Ser. No. 347,133, supra, the coefficient of friction is reduced to about 0.13. The coefficient of friction of the preferred coextruded lubricious coating of the invention is about 0.08.

The hydrophilic lubricating polymer absorbs water when the coating composition on the surface of the shaped base polymer contacts water. It is believed that the absorption of water causes the molecules of lubricating polymer to become mobile within the composition wherein some of the molecules migrate to the surface of the article. It is believed that the mobility of the lubricating polymer molecules on the article surface provides the lubricity.

The following examples are provided to further illustrate the invention but are not to be considered as limitative of the invention.

EXAMPLE I

General Procedure for Polyurethane Synthesis

The calculated quantities of polyqlycol and diol extender required to prepare a polyurethane having the desired hard segment content were combined in a resin bottle at 60° C., and vacuum stripped for 16 hours and 50°-55° C. at 1-2 mm Hg. The mixture was cooled to ambient temperature and the calculated amount of filtered diisocyanate, based on the total hydroxyl content, was added all at once with vigorous stirring. The exotherm reached about 80° C., whereupon the mixture was poured into a Teflon-lined tray and post-cured at 125° C. for about 60 minutes.

In an alternative procedure, the polyglycol and diisocyanate may be mixed with stirring, and, when the initial exotherm begins to subside, the extender may be added with continued stirring.

EXAMPLE II

General Procedure for Preparation of Coating Composition

The lubricious coating compositions were compounded in 7 lb. batches using a Banbury mixer. The resin components were weighed, dry mixed and put into the mixing chamber where they were compounded at 60 RPM. The mixing chamber temperature was maintained between 150° and 190° F. The mixture was allowed to flux for 3 to 5 minutes, and then the rotor speed was reduced to 20 RPM and the jacketed mixing chamber was chilled with water. At approximately 130° F., the mixture was taken out of the mixing chamber and allowed to cool to room temperature. The composition was immersed in liquid nitrogen and then granulated on a Foremost Model SHD-1 grinder. The chipped composition was dried prior to the coextrusion runs.

EXAMPLE III

General Procedure for Coextrusion

A base polymer melt stream from a main extruder and a coating composition melt stream from a coextruder were maintained separately until combined in the forward, down stream portion of an extruder head. From the extruder head, the streams subsequently passed through and emerged from a tubing die (coaxial or cross-head) as an integral tubing member having the coating composition laminated on a surface of the base polymer tubing.

Representative processing conditions are as follows using a Genca Tri-Die System without gear pumps or screen packs.

|  | Base PVC | Coating Composition |
|---|---|---|
| Extruder (L/D 24:1) | 1" Killion | ¾" Killion |
| Feed Throat | Non-grooved | Non-grooved |
| Temperatures, °F. |  |  |
| Zone 1 | 310 | 250 |
| Zone 2 | 355 | 305 |
| Zone 3 | 370 | 335 |
| Die 1 | 370 | 355 |
| Melt Temperature, °F. | 363 | — |
| Barrel Pressure, PSI | 1000 | 485 |
| Screw RPM (setting) | 25 | 15 |
| Extruder Amperage | 4.4 | 0.6 |
| Puller Speed | 18 | — |
| Air Gap | ¾" |  |

By proper selection of extruders, coextruders and dies, a tubing may be obtained having a laminated layer of coating composition on either or both of the outside and lumen surfaces of the base polymer tubing.

EXAMPLE IV

Lubricity Testing

The lubricity of the disclosed coated tubings were evaluated by comparing the surface coefficients of friction of the coated samples with that of the uncoated substrate. Surface coefficients of friction were determined using an Instron Universal Testing Machine, Model 1122, and the drag generated between the sample and a natural rubber substrate was measured. Test samples were secured in a water filled trough and were soaked for 5 minutes before testing. A piece of clean, pure, natural gum rubber (lab grade, Fisher Scientific) was placed in contact with the test sample under water and pulled at a constant speed (5 cm/min) under a standard applied load (532 gm). The measured drag force in newtons (N) was converted to the coefficient of friction (CF) using the following equation:

$$CF = \frac{\text{Drag Force }(N) - \text{Internal Friction }(N)}{0.0098\ (N/\text{gm}) \times \text{Applied Load (gm)}}$$

where the internal friction is the drag generated by the friction apparatus in the absence of sample contact.

What is claimed is:

1. A medical article which is lubricious when wet comprising a shaped polyvinyl chloride substrate and a coating thereon, said coating comprising a noncovalently bonded hydrophilic polymer and an alloy of polyvinyl chloride and polyurethane, said alloy serving as a carrier for said polymer and adhering to said substrate.

2. The article of claim 1 wherein said coating further comprises a homogenizing polyurethane to enhance the compatibility of said hydrophilic polymer and said alloy.

3. The article of claim 2 wherein said homogenizing polyurethane has a soft segment comprising polyethyleneoxide, polytetramethyleneoxide and mixtures thereof.

4. The article of claim 1 wherein said hydrophilic polymer is selected from the group consisting of polyethyleneoxide and a polyetherurethane having a polyethyleneoxide soft segment.

5. The article of claim 4 wherein said polyethyleneoxide has a molecular weight of about 100,000 to 8,000,000.

6. The article of claim 1 wherein said polyurethane is selected from the group consisting of a polyesterurethane, a polyetherurethane and a mixture thereof.

7. The article of claim 6 wherein said polyetherurethane has a soft segment comprising a polyglycol selected from the group consisting of polyethyleneoxide glycol, polypropyleneoxide glycol, polytetramethyleneoxide glycol and mixtures thereof.

8. The article of claim 6 wherein said polyesterurethane has a soft segment selected from the group consisting of polycaprolactone and polyethylene adipate.

9. The article of claim 1 which is a medical tubing.

10. A medical article which is lubricious when wet comprising a shaped base polymer and a coating thereon, said coating comprising a noncovalently bonded hydrophilic polymer and a polymeric carrier therefor, said polymeric carrier adhering to said base polymer.

11. The article of claim 10 wherein said base polymer is selected from the group consisting of polyvinylchloride, polyurethane, polyurethaneurea polyurethane-silicone block copolymer, polyolefin and mixtures thereof.

12. The article of claim 10 further comprising a radiopaque agent distributed in said base polymer.

13. A medical article which is lubricious when wet comprising a shaped polyvinylchloride tubing having a coating thereon, said coating comprising polyethyleneoxide, a homogenizing polyurethane and an alloy of a second polyurethane and polyvinylchloride, said alloy adhering to said tubing and said homogenizing polyurethane enhancing the compatibility of said alloy and said noncovalently bonded polyethyleneoxide.

14. The article of claim 13 wherein said homogenizing polyurethane is the product from reaction of 4,4'-diphenylmethane diisocyanate, butanediol, polytetramethyleneoxide glycol and polyethyleneoxide glycol.

15. The article of claim 13 wherein said second polyurethane is the product of reaction of 4,4'-diphenylmethane diisocyanate, butanediol and a polyglycol selected from the group consisting of a polyester glycol, a polyether glycol and a mixture thereof.

16. The article of claim 13 wherein the ratio of the components of said coating are about 70:20:10 parts by weight of said alloy, said homogenizing polyurethane and said polyethyleneoxide respectively.

17. A method for preparing a shaped medical article which is lubricious when wet comprising coextruding a melt of polyvinylchloride and a melt of a coating composition, said composition comprising a noncovalently bonded hydrophilic polymer and an alloy of polyvinylchloride and polyurethane to give a shaped polyvinylchloride article having thereon an adhered layer of said coating composition, said layer when wet absorbing water and becoming lubricious.

18. The method of claim 17 wherein said coating composition further comprises a homogenizing polyurethane to enhance the compatibility of said hydrophilic polymer and said alloy.

19. The method of claim 18 wherein said polyurethane has a soft segment comprising polyethyleneoxide, polytetramethyleneoxide and mixtures thereof.

20. The method of claim 17 wherein said hydrophilic polymer is selected from the group consisting of polyethyleneoxide and a polyetherurethane having a polyethyleneoxide soft segment.

21. The method of claim 17 wherein said polyurethane is selected from the group consisting of a polyesterurethane, a polyetherurethane and a mixture thereof.

22. A method for preparing a shaped medical article which is lubricious when wet comprising coextruding a melt of a base polymer and a melt of a coating composition, said composition comprising a hydrophilic polymer and a polymeric carrier therefor to give a shaped article of said base polymer having thereon an adhered layer of said coating composition, said layer when wet absorbing water and becoming lubricious.

23. The method of claim 22 wherein said base polymer is selected from the group consisting of polyvinylchloride, polyurethane, polyurethaneurea, polyurethane-silicone block copolymer, polyolefin and mixtures thereof.

24. A method for preparing a medical tubing which is lubricious when wet comprising coextruding a melt of polyvinylchloride and a melt of a coating composition, said composition comprising noncovalently bonded polyethyleneoxide, a homogenizing polyurethane and an alloy of polyvinylchloride and a second polyurethane to give a polyvinylchloride tubing having thereon an adhered layer of said coating composition, said layer when wet absorbing water and becoming lubricious.

* * * * *